United States Patent [19]

Watt

[11] 4,247,472
[45] Jan. 27, 1981

[54] METHOD FOR PRODUCING BIS-[4-(DIPHENYLSULFONIO)PHENYL] SULFIDE BIS-M.X6 PHOTOINITIATOR

[75] Inventor: William R. Watt, Princeton Junction, N.J.

[73] Assignee: American Can Company, Greenwich, Conn.

[21] Appl. No.: 59,188

[22] Filed: Jul. 19, 1979

Related U.S. Application Data

[62] Division of Ser. No. 20,340, Mar. 14, 1979, Pat. No. 4,201,640.

[51] Int. Cl.$^3$ .............................................. C07F 9/66
[52] U.S. Cl. .................................................. 260/440
[58] Field of Search .................. 260/606.5 P, 440, 446

[56] References Cited

U.S. PATENT DOCUMENTS

| | | | |
|---|---|---|---|
| 2,807,648 | 9/1957 | Pitt | 260/607 B |
| 3,259,660 | 7/1966 | Cisney | 260/607 B |
| 3,585,227 | 6/1971 | Dreyfuss | 260/606.5 F X |
| 3,981,897 | 7/1976 | Crivello | 260/606.5 P X |
| 4,069,054 | 1/1978 | Smith | 96/115 P |
| 4,069,055 | 1/1978 | Crivello | 96/115 R |
| 4,081,276 | 3/1978 | Crivello | 96/35.1 |
| 4,136,102 | 1/1979 | Crivello | 260/440 |
| 4,138,255 | 2/1979 | Crivello | 96/35.1 |
| 4,139,385 | 2/1979 | Crivello | 96/35.1 |
| 4,161,478 | 7/1979 | Crivello | 260/440 X |

Primary Examiner—Helen M. S. Sneed
Attorney, Agent, or Firm—Robert P. Auber; Stuart S. Bowie; Peter L. Costas

[57] ABSTRACT

A highly effective photoinitiator for cationic polymerization of monomer formulations is prepared by reacting bis-[4-(diphenylsulfonio)phenyl] sulfide bis-halide wherein halide is chloride or bromide in an aqueous solution with a compound having the formula T MF$_6$ wherein M is one of phosphorus, antimony or arsenic and T is hydrogen or a metal whose halide salt is water soluble. The two compounds react in the aqueous medium to produce a precipitate which includes at least about 50 percent by weight bis-[4-(diphenylsulfonio)phenyl] sulfide bis-MF$_6$, and this precipitate may be recovered and dried for utilization without further purification if so desired. Purification may be effected by dissolving the dried product in an organic solvent, cooling the solvent to precipitate the impurities, and thereafter recovering relatively pure bis-[d-(diphenylsulfonio)phenyl] sulfide bis-MF$_6$ by chilling the solvent solution to form a precipitate, and then separating and drying the precipitate. The preferred compounds are those wherein the substituent M is phosphorus so that the product comprises bis-[4-(diphenylsulfonio)phenyl] sulfide bis-hexafluorophosphate. The cationic polymerization processes utilize the photoinitiator in an amount equal to about 0.5–6.0 percent by weight of the monomer therein.

9 Claims, No Drawings

METHOD FOR PRODUCING BIS-[4-(DIPHENYLSULFONIO)PHENYL] SULFIDE BIS-M-X$_6$ PHOTOINITIATOR

CROSS REFERENCE TO RELATED APPLICATION

The present application is a division of my copending application Ser. No. 20,340 filed Mar. 14, 1979, now U.S. Letters Pat. No. 4,201,640.

BACKGROUND OF THE INVENTION

For a number of years, the polymer coating industry has been engaged in substantial development programs involving the identification or synthesis of various photoinitiators which would permit high speed curing of the polymerizable formulations following exposure to sources of electromagnetic radiation. This has been particularly true in various segments of the coating industry where it has been desired to eliminate the volatile solvents required in many polymer coating processes because of the potential hazards or because of the cost of the equipment to handle the evolved solvent vapors. However, the industry has long recognized the necessity to provide polymerizable compositions which would exhibit relatively long pot life and/or shelf stability prior to exposure to the source of electromagnetic radiation.

In William R. Watt U.S. Pat. No. 3,794,576 granted Feb. 26, 1974, there are described and claimed certain highly advantageous epoxy coating formulations which combine the desired rheological properties with suitable pot life and rapid curing. The formulations therein utilize as the photoinitiator diazonium salts which decompose upon irradiation by ultraviolet light to produce rapid curing of the coating to a tack-free condition. As explained in detail therein, the desired rapid curing of the epoxy formulations requires that they contain at least about 15 percent by weight of an epoxidic ester with two epoxycycloalkyl groups.

Since the disclosure of the Watt Patent, there have appeared a number of patents and publications disclosing onium catalysts effective to replace the diazonium catalysts specifically described in the Watt Patent. These onium catalysts are described in detail in Barton U.S. Pat. No. 4,090,936 granted May 23, 1978, and Crivello U.S. Pat. Nos. 4,069,055 granted Jan. 17, 1978 and 4,058,401 granted Nov. 15, 1977. The mechanism and operation of the triaryl sulfonium salts is described in detail in Crivello et al "Triaryl Sulfonium Salts: A New Class of Photoinitiators for Cationic Polymerization", JOURNAL OF RADIATION CURING, Volume 5, pages 2, 10-11, January 1978, and "UV Curing: Science and Technology", edited by S. P. Pappas (Technology Marketing Corporation, Stamford, Connecticut).

Among the most popular of the sulfonium catalysts for epoxy polymerization and for other cationic polymerization is triphenyl sulfonium hexafluorophosphate. Many of the recent studies have centered upon the use of this photoinitiator. Although triphenyl sulfonium hexafluorophosphate offers certain advantages over the diazonium type catalysts from the standpoint of longer shelf life and rapid curing, it is generally a relatively expensive material which has a limited range of spectral sensitivity. Accordingly, there has continued to be a significant need for relatively low cost, high speed photoinitiators affording relatively broad spectral sensitivity to electromagnetic radiation and which would also exhibit highly desirable shelf life.

Accordingly, it is an object of the present invention to provide a novel process for producing a highly effective photoinitiator for cationic polymerization of various monomers.

It is also an object to provide such a process which enables utilization of relatively inexpensive and readily available reactants and which utilizes simple procedures for reaction and for purification if so desired.

SUMMARY OF THE INVENTION

It has now been found that the foregoing and related objects may be readily attained in a method in which a photoinitiator is prepared by a series of steps including the preparation of a first reactant comprising bis-[4-(diphenylsulfonio)phenyl] sulfide bis-halide wherein halide is chloride or bromide and admixing the first reactant in an aqueous solution with a second reactant having the formula T.MF$_6$ wherein M is one of phosphorus, antimony or arsenic, T is hydrogen or a metal whose halide salt is water-soluble. The two reactants in the aqueous medium react to produce a precipitate which includes at least about 50 percent by weight bis-[4-(diphenylsulfonio) phenyl] sulfide bis-MF$_6$ based upon solids content, and this precipitate is recovered and then dried, initially at a temperature below about 50° C. to obtain a frangible product. This product may then be dried further at a temperature of up to about 110° C.

To purify the crude product thus obtained, it is then dissolved in a solvent therefor selected from the group consisting of C$_1$–C$_3$ alcohols, C$_3$–C$_6$ ketones, and C$_2$–C$_6$ esters at an elevated temperature in excess of 50° C. and up to the boiling point of the solvent. The solvent solution is cooled to form an insoluble precipitate, and the supernatant solution is separated from the precipitate. The solution is then chilled to a temperature below about 10° C. effective to precipitate out a relatively pure product which is then recovered and dried to produce a photoinitiator comprising about 90–98 percent by weight bis-[4-(diphenylsulfonio) phenyl] sulfide bis-MF$_6$.

In the preferred embodiment of the present invention, the halide of the first reactant is chloride. The phenyl groups of the first reactant and accordingly of the photoinitiator are unsubstituted; alternatively, they may be halogen substituted. In the preferred embodiment, M is phosphorus and T is hydrogen or an alkali metal.

Desirably, the solvent is methanol and the temperature of the solution is lowered to between 0° and −25° C. to precipitate the relatively pure product. In dissolving the initial product in the methanol solvent, a temperature of 50° to 65° C. is employed.

DETAILED DESCRIPTION OF THE PREFERRED EMBODIMENTS

As previously indicated, the method of the present invention involves the reaction of two reactants in an aqueous medium to produce a precipitate which includes bis-[4-(diphenylsulfonio) phenyl] sulfide bis-MF$_6$ and this precipitate is subsequently dried and desirably purified to recover a photo-initiator which is substantially comprised of bis-[4-(diphenylsulfonio) phenyl] sulfide bis-MF$_6$.

The first reactant is bis-[4-(diphenylsulfonio)phenyl] sulfide bis-halide wherein halide is chloride or bromide and the phenyl groups thereof may be unsubstituted or they may be substituted with halogens. Such compounds are available commercially from various sources or they may be conveniently synthesized by known and conventional processes. Preferably, the reactant is relatively pure bis-[4-(diphenylsulfonio)phenyl] sulfide bis-halide wherein halide is chloride or bromide, and the preferred compounds are those where the halide is chlorine.

The second reactant is a compound having the formula $T.MF_6$ wherein T is hydrogen or a metal whose halide salt is water-soluble, and M is selected from the group consisting of one of phosphorus, antimony and arsenic. The preferred reactants are those wherein T is hydrogen or sodium or potassium and wherein M is phosphorus. Again, such compounds are available commercially, and they also may be synthesized readily.

The two reactants are admixed in an aqueous medium in which they are both soluble, preferably in a ratio of two moles of $TMF_6$ per mole of bis-[4-(diphenylsulfonio)phenyl] sulfide bis-halide wherein halide is chloride or bromide since their reaction is substantially quantitative. Although an excess of $T MF_6$ may be employed if so desired to ensure complete reaction of the bis-[4-(diphenylsulfonio)phenyl] sulfide bis-halide wherein halide is chloride or bromide, it must be appreciated that an excess of either reactant will be unused and therefore increase the costs of the process and the problems of purification.

The water into which the reactants are introduced must be of sufficient quantity to permit them to be dissolved therein and to permit the gelatinous precipitate which forms to be separated from the dissolved salts and other impurities. Generally, the amount of water may be within a broad range of 0.5-2.0 liters per mole of $T MF_6$ so long as the desired separation may be effected. The temperature of the water and thereby the temperature at which the reaction is conducted does not appear to be particularly significant either to the reaction itself or to the formation and nature of the gelatinous precipitate since no appreciable differences have been noted at temperatures ranging from 0° C. to 50° C. Stirring for a limited period of about 0.5-2.0 hours is desirable to ensure complete reaction. Since the reaction proceeds almost instantaneously, time is controlling only from the standpoint of permitting the gelatinous precipitate to form and to lose some of the water entrapped therein during its formation. Normally, a period of 0.5-2.0 hours following reaction is desirable for this purpose.

As indicated above, the gelatinous precipitate containing the product also includes a substantial volume of water which must be removed therefrom and the entrapped water may contain some of the undesired salts and impurities. Accordingly, preliminary steps to remove some of the water are desirable including vacuum filtration or filtration in a filter press.

The drying operation is quite critical since initial exposure to temperatures in excess of about 50° C. will convert the precipitated product to an amorphous, dark colored syrup which on cooling becomes a brittle, glass-like material which is very difficult to process further. Accordingly, the material should be dried in air or under vacuum slowly at ambient temperatures until the material becomes friable, i.e., breaks into a crumbly product when pressure is applied with a spatula or a rod; this will normally require a period of 12-36 hours. Following this initial drying, the temperature may be elevated to a temperature not exceeding about 110° C. for further drying during a period of about 4-18 hours; generally, a temperature of 100°-105° C. for a period of 6-8 hours is satisfactory. Dessicants such as phosphorus pentoxide are advantageously employed.

Although the product may be used in this state, it may be desirable to take further steps to effect purification to increase the amount of bis-[4-(diphenylsulfonio) phenyl] sulfide bis-$MF_6$ in the product. At this point, the bis-[4-(diphenylsulfonio) phenyl] sulfide bis-$MF_6$ content is about 50-60 percent of the solids and the impurities contained therein have not been found to significantly affect the qualities of the photoinitiator. However, further purification to increase the percentage of the photoinitiator in the product appears to increase the activity thereof and may afford other advantages.

In the further purification, the dried product is dissolved in a solvent therefor selected from the group consisting of $C_1$-$C_3$ alcohols, $C_3$-$C_6$ esters and $C_2$-$C_6$ ketones. Exemplary of such solvents are methanol, methyl ethyl ketone, acetone, ethyl acetate and cellosolve acetate; methanol is preferred because of its low cost and handling characteristics. To facilitate dissolution in the smallest volume possible, the solvent is preferably heated to a temperature approaching its boiling point; for example, the preferred methanol is heated to a temperature of about 50°-65° C. Since the solvent must subsequently be stripped, it is obviously desirable to limit the volume thereof, preferably to the minimum required; with methanol, about 10-15 parts will dissolve 1 part of the crude dried product at the above temperatures. A negligible amount of a dark gum may not dissolve.

Following dissolution of the crude product in the solvent, the solution is allowed to cool and the impurities settle out as a gum-like precipitate. The supernatant liquid is then separated from the precipitate and is desirably evaporated to about 40-60 percent of its original volume. The concentrated liquid is then chilled to a temperature below about 10° C., at which point the substantially pure product precipitates as a white solid. The temperature to which the liquid is chilled will vary with the solvent selected; for methanol, temperatures between $-5°$ and $-30°$ are desirable to effect precipitation of substantially all of the product while avoiding precipitation of impurities.

The solvent is then separated from the product by filtration while still chilled, and the product is then dried either in air or under vacuum at temperatures of up to about 110° C. for periods of 0.5-5.0 hours. The resulting product is normally about 90-98 percent pure bis-[4-(diphenylsulfonio) phenyl] sulfide bis-$MF_6$ with the remaining impurities apparently being active photoinitiators and non-interfering.

The bis-[4-(diphenylsulfonio) phenyl] sulfide bis-$MF_6$ photoinitiators produced by the present invention may be used to initiate polymerization of any cationically polymerizable monomer formulation including epoxide formulations, vinyl ethers, cyclic ethers and ketones, lactones and oxetanes, styrenes, acrolein, vinylarenes such as 4-vinyl biphenyl, vinyl cycloaliphatics such as vinylcyclohexene, isobutylene, dienes such as butadiene and isoprene, etc. The amount thereof incorporated in the polymerizable formulation will normally fall within the range of 0.5-6.0 percent by weight of the polymerizable monomers therein, and preferably about 1.0-4.0 percent.

The preferred polymerizable formulations are those in which epoxide monomers are present and preferably those epoxide formulations which contain at least about 15 percent by weight of prepolymer having two epoxycycloalkyl groups per molecule as will be described hereinafter. Alternatively, the epoxy formulation may be subjected to a controlled elevated temperature following exposure to radiation as will also be described hereinafter.

The epoxidic prepolymer materials which are preferred for the polymerizable formulations herein comprise any monomeric or oligomeric material containing at least one functional epoxy group or oxirane ring so that they may by polymerized upon opening of the oxirane ring. In addition, polymeric epoxy materials may be employed if they may be dispersed in the composition and are capable of undergoing further polymerization to produce a solid polymer. The epoxy compounds may be aliphatic, cycloaliphatic, aromatic or heterocyclic.

The epoxidic prepolymer should contain no functional groups more basic than the oxirane ring and should be a solvent for the initiator. Most desirably, the prepolymer should contain a reasonable percentage of epoxy compounds containing two or more epoxy groups per molecule.

The polymerizable epoxy material will be epoxide resins used either singly or in combination and will have an average epoxide value of about 0.1–1.0. The carbon chains having the epoxy groups may include additional substituents including ethers, esters, halogens, phosphates, and the like, and the compounds may include other polymerizable functional groups such as acrylates and silicones.

Typical epoxy materials are readily available commercially, the most common being those which are the product of bis-phenol A with epichlorohydrin or those resulting from the reaction of epichlorohydrin with a phenol/formaldehyde resin of relatively low molecular weight. Reference may be made to the HANDBOOK OF EPOXY RESINS by H. Lee and K. Neville (McGraw-Hill 1967) for various epoxides. In addition, the technical literature and patent literature both contain extensive discussions of various epoxidic prepolymer materials which are useful in the compositions of the present invention as will be demonstrated hereinafter.

In W. R. Watt U.S. Pat. No. 3,794,576, granted Feb. 26, 1974, there are described radiation-sensitive epoxidic blends containing at least about 15 percent by weight of an epoxidic ester having at least two epoxycycloalkyl groups per molecule in order to achieve rapid polymerization and curing of the composition rapidly upon exposure to ultraviolet radiation or the like. Such compounds are conveniently esters of an epoxidized cyclic alcohol and an epoxidized cycloalkanecarboxylic acid or esters of an alkyl-substituted (epoxycycloalkane)methanol and a dibasic acid. A number of suitable compounds are disclosed in the aforementioned Watt Patent. The advantage to the inclusion of the epoxycycloalkyl compounds is that polymerization of the formulation will take place rapidly following exposure to radiation and without requiring temperature acceleration.

Although not essential and sometimes undesirable, the polymerizable epoxy composition may contain diluents to improve viscosity, and these diluents may be reactive such as those produced by reaction of an alcohol or a phenol with epichlorohydrin. Exemplary of reactive diluents is the reaction product of nonylphenol with epicholorohydrin. The amount of diluent may vary from zero to as much as 45 percent of the composition if a reactive diluent is employed and is preferably less than 15 percent if nonreactive diluents such as dibutylphthalate are employed.

For some applications, the composition may contain an inert pigment or dye to provide a desired coloration. Generally, such pigments and dyes will comprise less than about 40 percent by weight of the composition. For certain applications, it may be desired to include an inert filler such as talc or silica, or polymers such as polyvinyl chloride, where such fillers will not adversely affect the desired properties for the cured composition. They wll normally comprise less than 60 percent by weight and preferably less than 25 percent by weight of the polymerizable composition.

The initiators of the present invention will decompose upon exposure to electromagnetic radiation so as to provide a Lewis acid which is effective to initiate polymerization of the cationically polymerizable composition. The term "Lewis acid" as used herein is intended to encompass compounds produced by decomposition and which will indirectly generate a Lewis acid to receive an electron pair from the monomer to initiate polymerization, as for example from the oxygen of the oxirane ring to open the oxirane ring. The classic Lewis acid precursor decomposition mechanism is described in the aforementioned Watt U.S. Pat. No. 3,794,576 with respect to a diazonium initiator.

The decomposition mechanism for triarylsulfonium salts to provide an indirectly formed Lewis acid has been postulated by Crivello et al in "Triarylsulfonium Salts: A New Class of Photoinitiators for Cationic Polymerization" in JOURNAL OF RADIATION CURING, Vol. 5, page 2 (January 1978). The authors postulate that the decomposition of the diaryl- and triarylsulfonium salts produce a Bronsted acid which in turn provides a proton which will function as the Lewis acid to accept electrons from an oxygen of an oxirane ring in an epoxide monomer and initiate polymerization in accordance with the following mechanism:

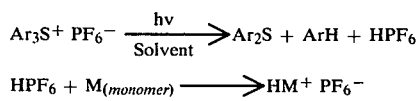

$$Ar_3S^+ \ PF_6^- \xrightarrow[\text{Solvent}]{h\nu} Ar_2S + ArH + HPF_6$$

$$HPF_6 + M_{(monomer)} \longrightarrow HM^+ \ PF_6^-$$

Regardless of the theory of the action embraced, it is apparent that the photoinitiator is decomposing to generate in the reaction medium an electron acceptor acting as a Lewis acid to open an oxirane ring in an epoxide compound or otherwise accepting an electron pair from other cationically polymerizable monomers and thereby initiating cationic polymerization of the monomer material. The reaction then proceeds as additional monomer units are activated until all of the monomer has been polymerized or until impurities interfere with the reaction mechanism.

As indicated, the photoinitiator is decomposed into a Lewis acid by exposure to electromagnetic radiation. Although electron beam bombardment, X-ray radiation, and other similar forms of high energy radiation may be employed for this purpose, exposure to ultraviolet radiation has been found highly satisfactory and is desirable for commercial applications. The exposure to radiation normally required may be of extremely short duration, periods of about one-half to three seconds being normally adequate for most compositions depending upon the intensity of the radiation at the surface.

However, for relatively thick deposits of the composition, it may be desirable to extend the period of exposure to four seconds or even more, to ensure adequate penetration of the radiation through the depth of the coating.

In the polymerization of epoxide prepolymer compositions which do not include the desirable epoxycycloalkyl compounds of the aforementioned Watt Patent to provide a rapid cure rate, it is possible to obtain rapid polymerization of at least the surface portion by maintaining the composition within a relatively narrow elevated temperature range for a period of 0.5–5.0 seconds following initiation of exposure to the electromagnetic radiation in order to achieve the desired rapid polymerization of the epoxide prepolymer material to a tack-free surface condition within a period of less than 30 seconds. Although this elevated temperature range may extend from 50° C. to as high as 90° C., it is generally held within the range of 55°–75° C. to obtain the desired rate of polymerization while avoiding adverse effects on the resulting polymer and the desired physical properties.

The temperature of the composition may be elevated to the desired temperature range by any suitable means including induction heating when a metallic substrate or container is employed; conductive heating; convection heating; and radiation heating by exposure to a source of suitable radiant heat such as infrared lamps. For convenience and for minimization of the equipment requirements, infrared radiation provided by suitable lamps is most desirably employed in conjunction with the source of ultraviolet radiation used to produce decomposition of the initiator.

The initiators of the present invention are particularly applicable to coating compositions for making durable coatings for either aesthetic or protective purposes. Epoxy compositions find particular advantage in the field of graphic arts because of the resistance of the coating to solvents and chemicals as well as to abrasion, because of the excellent adhesion to various surfaces including metals and because of the ability to withstand drawing and forming operations.

Illustrative of the various aspects of the methods of the present invention are the following specific examples wherein all examples are parts by weight unless otherwise indicated.

EXAMPLE ONE

To a liter of water are added 40 grams of potassium hexafluorophosphate with stirring to effect complete dissolution. To 5 liters of a water/ice slurry are added 130 grams of a 50 percent aqueous solution of a commercially purchased material comprising substantially bis-[4-(diphenylsulfonio)phenyl] sulfide bis-chloride.

The solution of potassium hexafluorophosphate is added dropwise with vigorous stirring to the water/ice slurry, and a voluminous white, creamy precipitate is formed. Stirring is continued for one hour as the precipitate increases in density. The mixture is then filtered on a vacuum filter. The gelatinous precipitate is placed in a vacuum oven containing phosphorous pentoxide as a dessicant and dried to constant weight at a temperature of 50° C.

The yield is found to be 84.4 grams. Analysis indicates the product to be about 50–60 percent bis-[4-(diphenylsulfonio) phenyl] sulfide bis-hexafluorophosphate. The product as formed by drying in the above phase is a frangible white powder and may be readily dissolved in polar solvents such as sulfolane and propylene carbonate.

An elemental analysis of the product indicates it to compare with the calculated values for bis-[4-(diphenylsulfonio) phenyl] sulfide bishexafluorophosphate:

| Element,% by wt. | Found | Calculated |
|---|---|---|
| Carbon | 51.2 | 51.0 |
| Hydrogen | 3.3 | 3.3 |
| Sulfur | 11.8 | 11.4 |
| Phosphorus | 6.6 | 7.3 |
| Fluorine | 26.9 | 26.9 |

Further purification of the product is effected in accordance with the following procedure.

The dried product is dissolved in boiling methanol in a ratio of 10 parts product to 100 parts by weight methanol. Following dissolution of the product, the solution is allowed to stand and cool to room temperature, at which point a brown to amber gum precipitates from the solution. The gum precipitate is removed from the solution and the supernatent liquid is evaporated to approximately 50 percent of its original volume. The evaporated solution is then chilled to a temperature of −15° C. at which point a white precipitate forms. The precipitate is filtered from the solution while the solution is still chilled and the precipitate is air dried on the filter. It is further dried in a vacuum oven at a temperature of approximately 100° C. until no further weight loss is observed.

Chromatographic analysis of the purified product indicates it to be approximately 95 percent pure bis-[4-(diphenylsulfonio) phenyl] sulfide bishexafluorophosphate. The purified product has a melting point within the range of 231°–238° C. Elemental analysis is compared with the calculated values for bis-[4-(diphenylsulfonio) phenyl] sulfide bis-hexafluorophosphate:

| Element,% by wt. | Found | Calculated |
|---|---|---|
| Carbon | 50.82 | 51.0 |
| Hydrogen | 3.22 | 3.3 |
| Sulfur | 11.36 | 11.4 |
| Phosphorus | 7.04 | 7.3 |
| Fluorine | 27.63 | 26.9 |

EXAMPLE TWO

To evaluate the activity of the photoinitiator produced in accordance with the present invention as compared with tri-phenylsulfonium hexafluorophosphate, several different epoxide formulations are prepared, aliquots of each formulation utilizing as the photoinitiator therein triphenyl sulfonium hexafluorophosphate (TPS), unpurified bis-[4-(diphenylsulfonio) phenyl] sulfide bis-hexafluorophosphate (BDS), or purified bis-[4-(diphenylsulfonio) phenyl] sulfide bis-hexafluorophosphate (BDS). In all instances, the photoinitiator is introduced as a 33 percent by weight solution in propylene carbonate.

| Component | Amount |
|---|---|
| FORMULATION I | |
| 3,4-epoxy cyclohexylmethyl-3,4-cyclohexane-carboxylate (sold by Ciba-Geigy under the designation CY-179) | 100.0 parts |
| Surfactant | 0.5 parts |
| Photoinitiator Solution | 6.0 parts |

| Component | Amount |
|---|---|
| FORMULATION II | |
| Bis-(3,4-epoxycyclohexylmethyl)adipate (sold by Union Carbide under the designation ERL 4299) | 100.0 parts |
| Surfactant | 0.5 parts |
| Photoinitiator Solution | 6.0 parts |
| FORMULATION III | |
| 3,4-epoxy cyclohexylmethyl-3,4-cyclohexane-carboxylate (sold by Ciba-Geigy under the designation CY-179) | 66.7 parts |
| Butanediol aliphatic diglycidyl ether (sold by Ciba-Geigy under the designation RD-2) | 33.3 parts |
| Surfactant | 0.5 parts |
| Photoinitiator Solution | 6.0 parts |
| FORMULATION IV | |
| 3,4-epoxy cyclohexylmethyl-3,4-cyclohexane-carboxylate (sold by Ciba-Geigy under the designation CY-179) | 80.0 parts |
| Epoxy ($C_{12}$–$C_{14}$ alkylglycidyl ether (sold by Procter and Gamble under the designation Epoxide #8) | 20.0 parts |
| Surfactant | 0.5 parts |
| Photoinitiator Solution | 6.0 parts |

The several epoxide formulations are applied to aluminum panels with a #4 wire wound rod and then placed upon a controlled temperature stage maintained at 30° C. Approximately 30 seconds is allowed for the coated panel to reach temperature equilibrium with the stage, after which it is exposed to a source of electromagnetic radiation. A ball of absorbent cotton is placed against the exposed coating to determine the time for the coating to become tack-free. The results of these tests are set forth in the following table:

| COMPARISON OF CURE RATES | | | |
|---|---|---|---|
| | | Tack-Free Time (Seconds) | |
| Formulation | Photoiniator | Following 2 seconds exposure to medium pressure mercury arc at 30° C. | Following 6 seconds exposure to 275-watt sunlamp at 30° C. |
| I | TPS | 5 | no cure |
| | Crude BDS | 1 | 1 |
| | Purified BDS | 1 | 1 |
| II | TPS | 6 | no cure |
| | Crude BDS | 4 | 4 |
| | Purified BDS | 3 | 3 |
| III | TPS | 9 | no cure |
| | Crude BDS | 3 | 4 |
| | Purified BDS | 2 | 3 |
| IV | TPS | 5 | no cure |
| | Crude BDS | 3 | 4 |
| | Purified BDS | 2 | 2 |

From the test data set forth in the table above, it can be seen that the photoinitiators produced by the method of the present invention offer significant advantages in improved cure rates as compared with triphenyl sulfonium hexafluorophosphate and also in greater sensitivity to sunlight. Other tests also indicate a response to light having wave lengths of greater than 300 nanometers which is significantly better than triphenyl sulfonium hexafluorophosphate and a better broad spectrum sensitivity than afforded by triphenyl sulfonium hexafluorophosphate.

Various tests conducted with respect to pot life indicate epoxy systems containing the photoinitiators produced by the method of the present invention exhibit significantly improved stability and accordingly, longer pot life.

As will be appreciated from an analysis of the method of the present invention, highly effective photoinitiators may be produced at relatively low cost as compared with triphenyl sulfonium hexafluorophosphate and other related onium photoinitiators. The starting materials are readily available and the procedures of the present invention are relatively simple and straightforward and involve substantially complete reaction of the components.

Thus, it can be seen from the foregoing detailed specification and examples that the novel methods of the present invention enable the preparation of a relatively economical and highly effective photoinitiator which exhibits improved spectral sensitivity as compared to triphenyl sulfonium hexafluorophosphate and affords significant advantages in cure rate. The methods utilize commercially available materials and are relatively simple. Since the product of the initial reaction following drying may be used without purification if so desired, even greater economies may be effected. Although the polymerizable compositions exhibit highly desirable shelf stability or pot life, polymerization proceeds rapidly following exposure to electromagnetic radiation.

Having thus described the invention, I claim:

1. In the method of making a photoinitiator, the steps comprising:

A. admixing a first reactant comprising bis-[4-diphenylsulfonio) phenyl] sulfide bis-halide wherein halide is chloride or bromide in aqueous solution with a second reactant having the formula $T.MF_6$ wherein M is one of phosphorus, antimony or arsenic, T is hydrogen or a metal whose halide salt is water soluble, said reactants reacting to produce a precipitate substantially comprising bis-[4-(diphenylsulfonio) phenyl] sulfide bis-$MF_6$, said second reactant being present in an amount of at least about 2 moles per mole of said solution providing about 0.5–2.0 moles water per mole of said second reactant, said reactants being admixed in said aqueous solution at a temperature of about 0°–50° C. for a period of time sufficient to permit said precipitate to form;

B. recovering said precipitate by separation from said solution; and

C. drying said precipitate at a temperature below about 50° C. for at least an initial period to dewater said precipitate and recover a frangible product containing at least 50 percent by weight bis-[4-(diphenylsulfonio) phenyl] sulfide bis-$MF_6$ based upon solids.

2. The method in accordance with claim 1 wherein said dewatered product is, subsequent to having reached a point where it is readily frangible, dried further at a temperature of up to 110° C.

3. The method in accordance with claim 1 including the further steps of:

A. dissolving the dried precipitate in a solvent therefor selected from the group consisting of $C_1$–$C_3$ alcohols, $C_3$–$C_6$ ketones, and $C_2$–$C_6$ esters at an elevated temperature in excess of 50° C. below the boiling point of said solvent;

B. cooling said solvent solution to form an insoluble precipitate;

C. separating said solution from said precipitate;

D. lowering the temperature of the solution to below about 10° C. effective to precipitate out substantially pure product;

E. recovering the precipitate; and

F. drying the precipitate to produce a photoinitiator comprising substantially bis-[(diphenylsulfonio) phenyl] sulfide bis-$MF_6$.

4. The method in accordance with claim 1 wherein said halide of said first reactant is chloride.

5. The method in accordance with claim 1 wherein said phenyl groups of said first reactant and of said photoinitiator are halogen substituted.

6. The method in accordance with claim 1 wherein said phenyl groups of said first reactant and of said photoinitiator are unsubstituted.

7. The method in accordance with claim 1 wherein M is phosphorus.

8. The method in accordance with claim 3 wherein said solvent is methanol and wherein the temperature of said solution is lowered between 0° C. and −25° C.

9. The method in accordance with claim 8 wherein the elevated temperature at which said precipitate is dissolved in methanol is within the range of 50°−65° C.

* * * * *